United States Patent [19]

Nyberg

[11] Patent Number: 4,764,343

[45] Date of Patent: Aug. 16, 1988

[54] OXYGEN SENSOR BASED ON OPTICAL DETECTION

[75] Inventor: Glen A. Nyberg, Warren, Mich.

[73] Assignee: General Motors Corporation, Detroit, Mich.

[21] Appl. No.: 930,517

[22] Filed: Nov. 14, 1986

[51] Int. Cl.$^4$ ............................................. G01N 21/78
[52] U.S. Cl. ...................................... 422/83; 422/91; 422/94; 422/98; 436/137; 356/445
[58] Field of Search .................. 73/23; 374/161, 162; 356/445, 446; 422/91, 94, 98, 83; 436/136–138, 164

[56] References Cited

U.S. PATENT DOCUMENTS

| | | | |
|---|---|---|---|
| 3,663,176 | 5/1972 | Cagle et al. | 23/232 R |
| 3,754,867 | 8/1973 | Guenther | 23/254 R |
| 3,920,402 | 11/1975 | Afanasieu et al. | 23/254 E |
| 4,032,297 | 6/1977 | Lyshkow | 23/254 E |
| 4,181,699 | 1/1980 | Kitzinger | 422/87 |
| 4,617,277 | 10/1986 | Bohl | 356/445 X |

Primary Examiner—Barry S. Richman
Assistant Examiner—Timothy M. McMahon
Attorney, Agent, or Firm—Domenica N. S. Hartman

[57] ABSTRACT

A gas sensing apparatus suitable for repeatedly sensing the partial pressure of a selected gas in a gaseous mixture is accomplished by employing optical detecting means. A sensing material having a light reflective surface reversibly reacts with a sensed gas in accordance with a temperature-sensed gas partial pressure relationship to cause a predictable change in reflectivity of the light reflective surface. The chemical reaction between the sensing material and sensed gas is reversible, therefore allowing quick, precise and repetitive sensed gas partial pressure determinations.

10 Claims, 1 Drawing Sheet

OXYGEN SENSOR BASED ON OPTICAL DETECTION

This invention generally relates to gas sensing apparatus which use optical detecting means for determining the concentration of a particular gaseous component in a gas mixture. In a specific embodiment, this invention relates to an apparatus suitable for optically detecting oxygen partial pressures in the exhaust gas of an automotive internal combustion engine operating with lean air-to-fuel ratios.

BACKGROUND OF THE INVENTION

Gas sensors are employed in a variety of applications requiring quantitative and qualitative gaseous determinations. In the automotive industry, it is well known that the oxygen concentration in the automobile exhaust has a direct relationship to the engine air-to-fuel ratio. Oxygen gas sensing devices are commonly employed within the internal combustion control system of the automobile to provide accurate exhaust gas oxygen concentration measurements for determination of optimum combustion conditions, maximization of efficient fuel usage, and management of exhaust emissions.

Typically, the oxygen sensors employed by the automotive industry are either electrochemical-type or resistive-type oxygen sensors. The electrochemical-type oxygen sensors are most common and comprise an ionically conductive solid electrolyte material, typically zirconia stabilized by the addition of yttria, a porous electrode coating on one face of the solid electrolyte contacting the external gas to be measured, and a porous electrode coating on the opposite face of the solid electrolyte contacting a known concentration of reference gas. The gas concentration gradient across the solid electrolyte produces a galvanic potential which is related to the differential of the partial pressures of the gas at the two electrodes. Resistive-type oxygen sensors generally comprise a layer of semiconductor oxide material which contacts the exhaust gas. The exchange of oxygen between the oxide's lattice and the exhaust gas causes the electronic resistivity of the oxide material to vary. This change in electrical resistance is related to the oxygen partial pressure of the exhaust gas.

These above mentioned electrochemical-type and resistive-type oxygen sensors are adequate for current automotive needs, which only require that the oxygen sensor determine qualitatively whether the internal combustion engine is operating at either of two conditions: (1) a fuel rich or (2) a fuel lean condition, as compared to stoichiometry. After equilibration, the exhaust gases from these two operating conditions have two widely different oxygen partial pressures. This information is provided to an air-to-fuel ratio control system, so that it can provide an average stoichiometric air-to-fuel ratio between the two conditions. However, due to the increasing demands for improved fuel utilization and emissions control, it is desirable to operate internal combustion engines exclusively within lean combustion parameters, i.e., air-to-fuel ratios between 15:1 and 25:1, where changes in the after-combustion oxygen partial pressures are comparatively slight and gradual. The galvanic-type and resistive-type oxygen sensors currently in widespread use are not sensitive enough for this operating environment.

I propose making a more sensitive oxygen sensor, that functions by optical detection means. Gas sensors using optical detection means to sense a desired gaseous component within a gas mixture are also known, and are generally used to detect the presence of a pollutant or toxic substance. Typically these prior optical-type gas sensors comprise a surface coated with an indicating material, the indicating material capable of producing a color change when contacted with the desired gaseous component. The color change is related to the concentration of the desired component in the gaseous mixture. A photoelectric device, or other similar means, detects the change in color and generates an electric signal proportionate to the color change and indicative of the gas concentration.

These optical-type gas sensors are useful when sensing the presence of an undesired component. However, they are not suitable for automotive use. They are typically bulky, have relatively slow response times, and are generally capable of only one determination of the desired gaseous component, since the chemical reaction causing the color change is typically not reversible.

To be an effective component of an automobile internal combustion control system operating exclusively within lean combustion conditions, the oxygen sensor must be extremely sensitive and capable of rapid, precise, and continuous (i.e., repetitive) oxygen concentration measurements. It is desirable that the response time of the sensor be less than 0.1 second at a minimum temperature of 300° C. and a maximum oxygen concentration at the sensing medium of about eight percent. Further, it is necessary that the oxygen sensor withstand high temperatures. It is also desired that the oxygen sensor be compact, yet structurally durable to withstand the harsh automotive environment.

SUMMARY OF THE INVENTION

It is an object of this invention to provide an improved gas sensing device capable of continuous, rapid, and precise measurements. It is a further object of this invention that the gas sensing device optically detect the change in reflectivity resulting from a reversible metal-to-metal oxide transformation, in order to determine the concentration of the desired gaseous component. One specific object of this invention is to provide a gas sensing device for detecting oxygen partial pressures within the exhaust gas from an internal combustion engine operating exclusively within lean combustion conditions, i.e., air-to-fuel ratios greater than 15:1.

This invention comprehends an optical gas sensing apparatus which includes a sensing material having a light reflective surface, temperature sensing means for the light reflective surface, light source means, optical heat source means, and light detecting means. The light reflective surface reversibly reacts with the sensed gas, in accordance with a known temperature-sensed gas partial pressure relationship, to cause a predictable change in reflectivity of the light reflective surface. The gas sensing apparatus is suitable for repeatedly sensing the partial pressure of a selected gaseous component in a gas mixture.

In accordance with a preferred embodiment of this invention, these and other objects and advantages of our invention will be better appreciated from the detailed description thereof which follows.

DETAILED DESCRIPTION OF THE INVENTION

Figure 1:
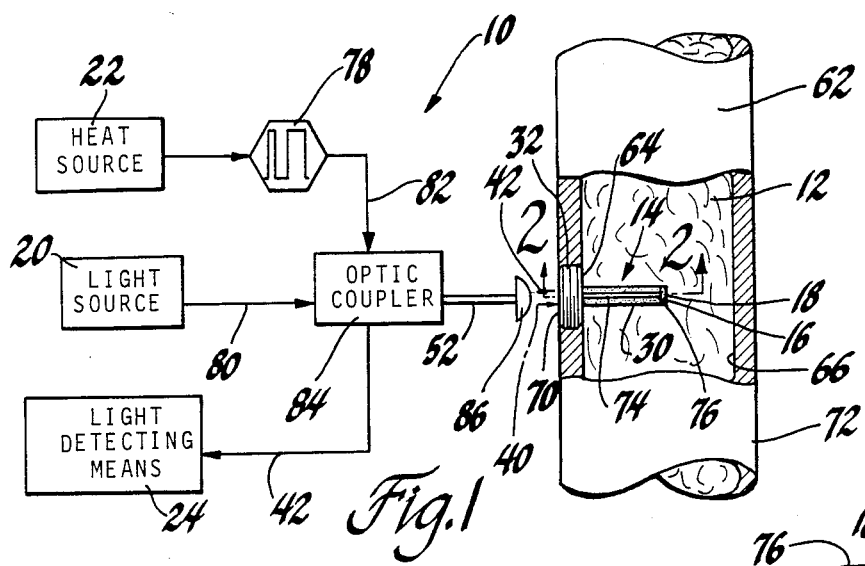
FIG. 1 is an overall illustration of the optical gas sensing apparatus in accordance with this invention.

This invention comprehends an optical gas sensing apparatus suitable for detecting oxygen partial pressures within automobile exhaust gas from an internal combustion engine operating with lean air-to-fuel ratios. The optical sensing apparatus includes a sensing material having a light reflective surface, temperature sensing means for the light reflective surface, light source means, optical heat source means, and light detecting means.

The light reflective surface comprises the sensing material. The metal sensing material reversibly reacts with the gas to be measured in a characteristic manner that is a function of temperature and sensed gas partial pressure, hereinafter referred to as the transformation temperature and transformation pressure respectively. The reaction corresponds to the phase transformation curve of the metal with that gas. Since the phase transformation equation for the metal with the gas to be sensed defines a curve, there is a continuum of transformation temperatures and transformation pressures along the curve. At any fixed transformation temperature and corresponding transformation gas partial pressure, both the metal and the reacted metal phase will be in equilibrium. The phase transformation is reversible, so that at those same transformation temperatures and pressures, the reacted metal will reversibly react with the gas to chemically transform to the metal. This phase transformation from metal to metal oxide results in a significant change in reflectivity of the light reflective surface comprising the metal sensing layer. In this invention, the metal sensing layer is palladium and forms palladium oxide when contacted with oxygen at the transformation partial pressure and temperature. The transformation is a reversible chemical reaction.

Temperature sensing means are preferably provided directly on the light reflective surface for detecting the temperature of the light reflective surface at two or more distinct locations on the light reflective surface. The light reflective sensing apparatus may be operated in at least two different modes, both modes of operation requiring precise temperature control of the light reflective surface. For any given transformation pressure, there will exist a unique transformation temperature. Therefore, if a thermal gradient, the thermal gradient spanning the range of transformation temperatures corresponding to the operational pressures of the gas to be sensed, is maintained along the light reflective surface, then for any operational gas partial pressure, there will exist a corresponding transformation temperature along the thermal gradient on the light reflective surface. All portions of the metal sensing material comprising the light reflective surface which are at a temperature less than the transformation temperature will be in a reacted, or oxidized, state. Therefore, an interface between the metal and the reacted metal phase exists at that location on the light reflective surface along the thermal gradient which is at the transformation temperature.

In the first mode of operation of this invention, the interface between the metal sensing material and reacted metal phase remains fixed, i.e., the reflectivity of the light reflective surface remains substantially constant. This is accomplished by precisely varying the temperature of the metal sensing material comprising the light reflective surface as the partial pressure of the gas to be sensed in the gaseous mixtures varies. The amount of heat required to vary the temperature of the light reflective surface so that the reflectivity of the light reflective surface remains substantially constant is related to the partial pressure of the gas to be sensed.

The second mode of operation of this invention requires that a constant temperature gradient is maintained along the metal sensing material comprising the light reflective surface. The temperature gradient spans the transformation temperatures corresponding to the transformation gas partial pressures which will exist during operation of the device. In this mode of operation, the temperature gradient across the metal sensing material comprising the light reflective surface remains substantially constant. If the gradient is circular, the interface between the metal and reacted metal phase contracts or dilates as the partial pressure of the gas to be sensed varies. For any operational partial pressure of the gas, the corresponding transformation temperature is represented on the light reflective surface along the circular temperature gradient. At that particular transformation temperature, represented by a circle along the thermal gradient on the light reflective surface, the metal and reacted metal phase will be in equilibrium forming an interface between the higher temperature, i.e., all metal, region and the lower temperature, i.e., all reacted metal phase, region. Therefore, as the partial pressure of the gas to be sensed varies, the corresponding transformation temperature varies, causing the circular boundary between the metal sensing material and the reacted metal phase to contract or dilate along the thermal gradient.

A light source means is positioned to shine a beam of light at the light reflective surface. The optical heat source means is positioned and modulated to provide controlled amounts of heat to the light reflective surface in order to control the temperature of the metal sensing material comprising the light reflective surface. The light detecting means is positioned to sense the reflected light from the light reflective surface. Fiber optic technology can be employed to transmit, focus, and delineate these three optical beams.

This invention produces an optical sensing device suitable for use in environments requiring repeated, rapid, and precise gas concentration measurements.

In the preferred embodiment of this invention, an optical gas sensing apparatus 10 detects the oxygen partial pressure in exhaust gas 12 from an automobile internal combustion engine operating with lean air-to-fuel ratios, i.e., air-to-fuel ratios ranging between 15:1 and 25:1. The optical gas sensing apparatus 10, as shown in FIG. 1, comprises a sensing probe 14 with a light reflective surface 16 comprising a metal sensing material 18, a light source means 20 to irradiate the light reflective surface 16, an optical heat source means 22 to provide heat to the light reflective surface 16, and a light detecting means 24 to sense the reflected light from the light reflective surface 16. Fiber optics technology is employed to transmit the three light beams.

Figure 2:
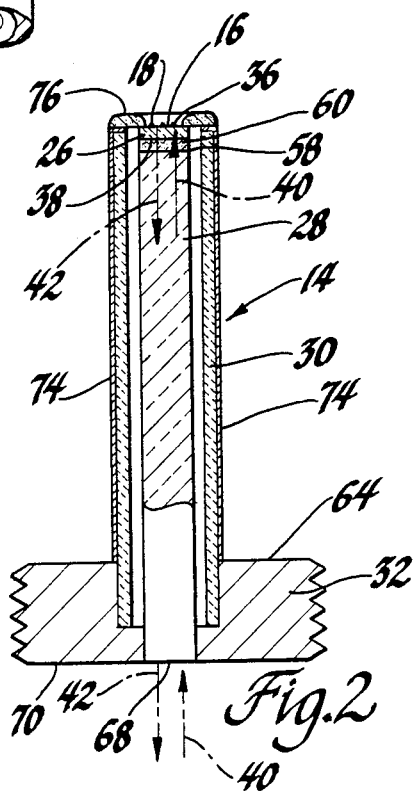
FIG. 2 is a cross-sectional view of the sensing probe comprised within the optical gas sensing apparatus in accordance with a preferred embodiment of this invention.

The sensing probe 14, as shown in FIG. 2, contacts the exhaust gas 12 and comprises a light reflective surface 16, a transparent or translucent substrate 26 to provide support for the light reflective surface 16, an optical fiber 28, a protective tube 30, and a base plate 32 that attaches to the exhaust pipe 62 of an automobile.

Figure 3:
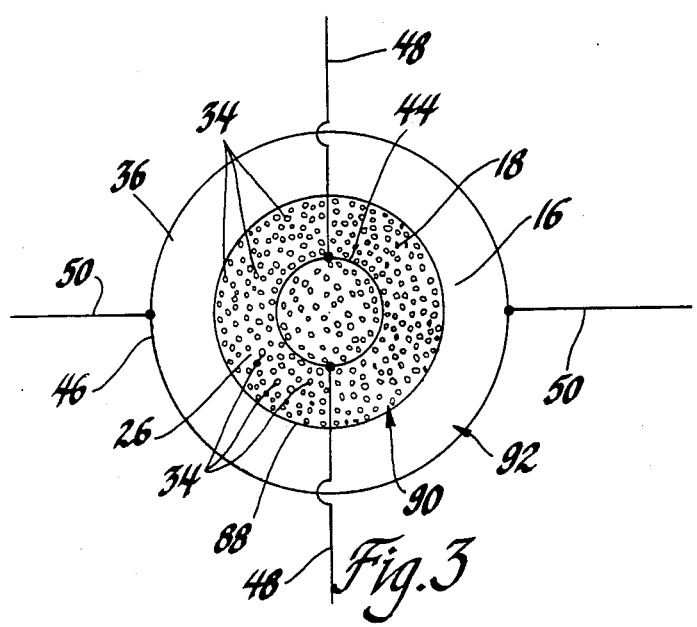
FIG. 3 is a diagrammatic view of the light reflective surface comprising the metal sensing material in accordance with a preferred embodiment of this invention.

The light reflective surface 16, about 200 microns in diameter, comprises a thin film layer of palladium metal, also referred to as the sensing layer 18, as shown in FIG. 3. In the preferred embodiment of this invention, the palladium metal 34 is deposited onto the supporting substrate 26 so as to form sparsely distributed, thin film clusters of palladium metal 34, about 100 Angstroms in diameter and about 15 Angstroms thick, on the supporting substrate 26. Palladium will naturally coalesce upon condensation to form this cluster configuration when it is deposited to such minimal thicknesses as here. The palladium clusters 34 cover approximately one to ten percent of the available surface area on the supporting substrate 26. Although the preferred embodiment discloses sparsely distributed palladium clusters 34, adequate results have been observed even when the palladium clusters 34 cover almost completely the available surface area on the supporting substrate 26. The palladium metal 34 is deposited using conventional thin film sputtering techniques or chemically by employing conventional washcoat methods used for applying catalytic materials to automotive catalytic converters. The deposition parameters are controlled so that the deposited palladium clusters 34 are light reflective.

A specular sensing layer 18 is most desirable. However, as a practical matter, complete specularity may not be feasible due to the costs of producing a specular layer. This invention does not require the use of a specular sensing layer; therefore, rough, or even porous, surfaces may be used as the sensing layer 18 on the supporting substrate 26. It is important, though, that the substrate 26 be substantially, i.e., greater than 80 percent, transmissive to the wavelength of radiation being reflected.

Figure 4:
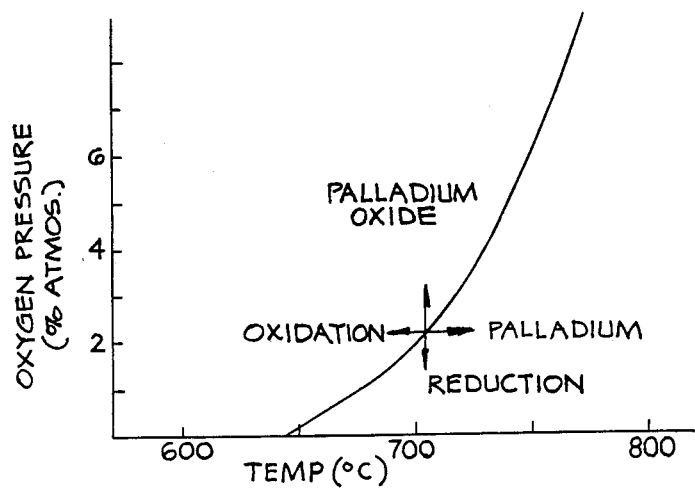
FIG. 4 illustrates the transformation curve for palladium metal and oxygen at temperatures and oxygen partial pressures corresponding to the temperatures and oxygen partial pressures of exhaust gas during lean operation of an internal combustion engine.

Palladium is the preferred material for the sensing layer 18 because of its naturally occurring advantageous properties. Palladium metal is inherently light reflective when suitably deposited. Palladium responds very rapidly to the presence of oxygen, due to its catalytic ability to react with oxygen gas. Also, the temperatures and oxygen partial pressures at which the reversible transformation of palladium with oxygen gas occurs, coincide very closely with the temperatures and oxygen partial pressures found in lean automotive exhaust gas, as shown in FIG. 4. In addition, the transformation of palladium and oxygen gas is reversible, allowing repetitive oxygen concentration measurements. Palladium is the preferred material for the sensing layer; however, adequate results may also be obtained when palladium alloys, such as a palladium-silver alloy, are used as the material for the sensing layer.

The sensing layer 18 which comprises the palladium film 34 is supported by a transparent or translucent glass substrate 26, about 200 microns in diameter and about 50 microns thick. Preferably, the supporting substrate 26 comprises fused silica so that the resulting substrate is transparent or translucent. The sensing layer 18 comprising the palladium clusters 34 is deposited on the exterior side 36 of the transparent supporting substrate 26, i.e., the side of the substrate 26 which contacts the exhaust gases 12. The interior side 38 of the substrate 26 is the side of the substrate 26 which receives the focused light beams 40. Therefore, the focused light beams 40 enter the substrate 26 at the interior side 38 of the substrate 26 and pass through the thickness of the substrate 26 before contacting the sensing layer 18. The light beams 42 reflected from the sensing layer 18 pass through the thickness of the substrate 26 prior to exiting the substrate 26 from the interior side 38 of the substrate 26 en route to the light detecting means 24.

Platinum resistance thermometers 44 and 46 are provided in the same plane as the palladium clusters 34 comprising the sensing layer 18 on the light reflective surface 16. The platinum resistance thermometers 44 and 46 are deposited using conventional thin film deposition techniques to form at least two concentric circular rings, an inner 44 and outer ring 46. An inner circular ring 44, about 53 microns outer diameter, about 48 microns inner diameter, and about 50 Angstroms thick, is deposited onto the exterior side 36 of the supporting substrate 26. Electrical leads 48 and 50 are provided from the inner ring 44 to the external electrical connections (not shown). The second platinum resistance thermometer 46 is provided by an outer ring 46, about 153 microns outer diameter, about 148 microns inner diameter, and about 50 Angstroms thick, which is deposited using conventional thin film deposition techniques. Electrical leads 50 are provided from the outer ring 46 to the external electrical connections (not shown).

An optical fiber 28 comprising a transparent fused silica core and cladding, about 200 microns in diameter and about one centimeter long, transmits the focused light beams 40 being provided to the light reflective surface 16 and also the light beams 42 reflected from the light reflective surface 16. (The figures are not to scale for clarity purposes.) The interior side 38 of the transparent supporting substrate 26 is bonded to the tip 58 of the optical fiber 28 using a layer of a conventional transparent binder 60, such as a lithium borosilicate glass binder. The supporting substrate 26 is positioned so that the focused light beams 40 transmitted through the optical fiber 28 from the light source means 20 and heat source means 22, enter through the interior side 38 of the supporting substrate 26 before passing through the supporting substrate 26 and contacting the light reflective surface 16. Reflected light 42 from the light reflective surface 16 passes through the supporting substrate 26 and exits at the interior side 38 of the substrate 26 before being transmitted through the optical fiber 28.

A protective tube 30, preferably comprised of hot-pressed silica powder, surrounds the optical fiber 28 and supporting substrate 26 comprising the light reflective surface 16. The tube 30 is about one centimeter long, with an outer diameter of about 1.1 centimeters and an inner diameter of about 0.9 centimeter. The silica tube 30 is positioned so that the tube 30 is flush with the tip 58 of the optical fiber 28 and substrate 26, the thickness of substrate 26 and binder 60 being exaggerated for clarity in FIG. 2. The silica tube 30 is supported by a stainless steel base plate 32, about four centimeters in diameter, which screws into the exhaust pipe 62 of the automobile. The thickness of the base plate 32 varies in accordance with the thickness of the exhaust pipe 62; however, the thickness is typically about one millimeter.

A hole is provided in the center of the base plate 32 through the thickness of base plate 32, so that the optical fiber 28 may feed through the base plate 32, and also to provide fixturing means for the ceramic tube 30. The center hole is machined so that the hole diameter is about 1.1 centimeters at the interior side 64 of the base plate 32. The interior side 64 of the base plate 32 is the side which is positioned about flush with the inner diameter 66 of the exhaust pipe 62 and contacts the exhaust gases 12. The approximate 1.1 centimeter hole is machined through only about 0.8 millimeter of thickness of the base plate 32. An interference fit between the ceramic tube 30 and base plate 32 is utilized to fixture the ceramic tube 30. The center hole is machined to a diameter of about 200 microns through the remaining thickness of the base plate 32, about 0.2 micron, in order to center and support the optical fiber 28. Therefore, the opposite end 68 of the optical fiber 28 from the tip 58 of the optical fiber 28 comprising the supporting substrate 26 is positioned about flush with the exterior side 70 of the base plate 32; i.e., the side of the base plate 32 which is flush with the outer diameter 72 of the exhaust pipe 62 and which does not contact the exhaust gases 12.

Electrically conductive stripes 74, comprising platinum or any suitable electrically conductive material, are applied to the exterior of the ceramic tube 30 in order to provide electrical connections to external electrical measuring equipment (not shown). The platinum resistance thermometers 44 and 46 comprised on the light reflective surface 16 are electrically connected to the electrically conductive platinum stripes 74 on the exterior of the ceramic tube 30 with conventional wire leads or electrically conductive platinum paste 76, such as platinum-based conducting paste, type 6082 from Englehard Corporation.

Although the preferred embodiment of the sensing probe 14 discloses using a silica based material for the supporting substrate 26, optical fiber 28, transparent binder 60, and protective tube 30, other suitable materials, such as alumina in a transparent or translucent form, may also be used for these components.

An electrically modulated light source means 20, such as a 600 nanometer wavelength, 100 microwatt light emitting diode with a one kiloHertz signal, is provided to irradiate the light reflective surface 16. Heat is provided to the light reflective surface 16 by optical heat source means 22, such as a conventional 20 watt lightbulb. A modulator 78 is provided so that the amount of heat being provided to the light reflective surface 16 can be controlled. Although a modulator is depicted in FIG. 1, other suitable means may be used to control the amount of heat provided to the light reflective surface, such as a light chopper, i.e., an electrically powered disc with slots, or a variable resistor in series with the lamp circuit that adjusts the voltage applied to the lightbulb filament. The heat source means 22 provides the heat to the light reflective surface 16, while the platinum resistance thermometers 44 and 46 comprised on the light reflective surface 16 measure the temperature of the light reflective surface 16 and communicate that data to external electrical measuring equipment (not shown).

The light beam 80 emanating from the light source means 20 and the light beam 82 emanating from the heat source means 22, also referred to as the incoming beams of light, are transmitted through optical fibers, such as commercially available multimode optical fiber comprising a glass core and glass cladding, to pass concurrently through a fiber optic coupler device 84, such as the 3-to-1 optical coupler from CANSTAR, Inc. These incoming light beams 80 and 82 are then transmitted through an optical fiber 52 of the same type used to transmit the incoming beams of light from the light source means and the heat source means, about one millimeter in diameter, and subsequently the beams are transmitted through a fiber optic focusing system 86 comprising two three-millimeter focusing lenses spaced appropriately or other suitable focusing means. The fiber optic focusing system 86 focuses the incoming beams of light 80 and 82, so that the focused beams of light 40 may be transmitted through the optical fiber 28, about 200 microns diameter, comprised within the sensing probe 14.

Light detecting means 24, such as a silicon photodetector device filtered to measure the one kiloHertz signal emitted from the light source means, sense the reflected light beams 42 from the irradiated light reflective surface 16. The reflected light 42 from the light reflective surface 16 passes through the supporting substrate 26, exits the interior side 38 of the supporting substrate 26, and then is transmitted through the optical fiber 28 of the sensing probe 14. The reflected light beam 42 then enters and passes through the fiber optic focusing system 86 and optical fiber 52 used to transmit the incoming beams of light 54. The fiber optic 3-to-1 coupler device 84 delineates the reflected light beam 42 from the incoming light beams 80 and 82 and transmits the reflected light beam 42 through an optical fiber, of the same type used to transmit the light beams emanating from the light source means and the heat source means, to the light detecting means 24.

The actual devices employed as the light source means 20, heat source means 22, and light detecting means 24, as well as the fiber optic coupler device 84 and focusing system 86, may be any suitable devices, as they form no part of the claimed invention.

This invention may be operated in at least two different modes. The sensing layer 18 comprised of palladium metal reversibly reacts with the gas to be sensed, i.e., oxygen gas, at temperatures and gas partial pressures corresponding to the phase transformation curve of palladium metal and oxygen gas, as depicted in FIG. 4, and also referred to as the transformation temperature and transformation pressure. A contiuum of transformation temperatures and transformation gas partial pressures exists along the transformation curve. At the transformation conditions, both the metal and reacted oxidized metal phase will be in equilibrium. The palladium-to-palladium oxide phase transformation is reversible, therefore at the transformation conditions, the reacted palladium will reversibly react with the oxygen to chemically transform back to palladium metal. The reaction reversibly proceeds in the opposite direction also at the transformation conditions. The reversible phase transformation from palladium-to-palladium oxide results in a significant change in the reflectivity of the light reflective surface 16 comprising the sensing layer 18.

Both modes of operation of this invention 10 require precise temperature control. For any given transformation temperature, there will exist a unique transformation gas partial pressure. Therefore, a thermal gradient, measured by the inner and outer platinum resistance thermometers 44 and 46 provided on the light reflective surface 16, spanning the range of transformation temperatures, about 650° C. to about 800° C., corresponding to the oxygen partial pressures within lean automotive exhaust, about 0.01 to about 0.08 atmospheres, is maintained along the light reflective surface 16. For any oxygen partial pressure existing during lean automotive internal combustion engine operation, there will exist a corresponding transformation temperature along the thermal gradient on the light reflective surface 16. All particles of the palladium sensing layer 18 at a temperature less than the transformation temperature will be in a reacted, or oxidized, state. Therefore, an interface 88, or circular boundary, between the unreacted palladium 90 and reacted palladium oxide 92 exists at that location on the light reflective surface 16 along the circular thermal gradient which is at the transformation temperature corresponding to the operational oxygen partial pressure of the exhaust 12.

In the first and more preferred mode of operation of this invention, the circular interface 88 between the unreacted palladium 90 and reacted palladium oxide 92 remains fixed, i.e., the reflectivity of the light reflective surface 16 remains constant. This is accomplished by precisely varying the temperature of the sensing layer 18 and the thermal gradient along the sensing layer 18, so that as the oxygen partial pressure varies, the corresponding transformation temperature remains at the interface 88 between the two metal phases. The amount of heat, which is provided by the heat source means 22, required to vary the temperature of the light reflective surface 16 so that the reflectivity of the light reflective surface 16 remains constant is related to the oxygen partial pressure in the exhaust gas 12.

The second mode of operation of this invention requires that a constant thermal gradient be maintained along the palladium sensing layer 18 comprising the light reflective surface 16. The thermal gradient spans the corresponding transformation temperatures of the oxygen partial pressures in the exhaust gas during lean internal combustion conditions. The thermal gradient along the light reflective surface 16 is circular and remains constant. Therefore, as the oxygen partial pressure varies, the corresonding transformation temperature varies, causing the circular interface 88 between the unreacted palladium metal 90 and the reacted palladium oxide 92 to contract or dilate along the thermal gradient on the light reflective surface 16. The change in reflectivity of the light reflective surface 16 is related to the oxygen partial pressure of the exhaust gas 12.

Although our invention discloses a preferred embodiment suitable for use as an oxygen partial pressure detector of exhaust gases within an automobile internal combustion engine control system, it is to be understood that various modifications and changes can be made in construction and use, such as a modification in the gas to be sensed, reversible sensing material, fiber optic technology, or dimensions of this invention, without departing from the spirit of the invention.

The embodiments of the invention in which an exclusive property or privilege is claimed are defined as follows:

1. An optical sensing apparatus, for repeatedly sensing the partial pressure of a selected gaseous component in a gas mixture, comprising:
    a film of heat responsive sensing material having a light reflective surface which reversibly reacts with a sensed gas in accordance with a temperature-sensed gas partial pressure relationship to cause a predictable change in reflectivity of the light reflective surface;
    temperature sensing means for detecting the temperature of the light reflective surface at two or more distinct locations on the light reflective surface;
    light source means for irradiating the light reflective surface, with a light beam from said light source means perpendicular to the light reflective surface;
    heat source means for providing a thermal gradient on the light reflective surface by means of a light beam transmitted from said heat source means perpendicular to the light reflective surface; and
    light detecting means for sensing reflection of the light irradiated on the light reflective surface from the light source means, said sensed reflection being transmitted perpendicular from the light reflective surface.

2. An optical oxygen sensing device for repeatedly sensing the oxygen partial pressure within automobile exhaust gases, comprising:
    a film of an oxidizable material having a light reflective surface which reversibly reacts with oxygen gas in accordance with a temperature-oxygen partial pressure relationship to form an oxide of said material on said light reflective surface, the oxidation of said material causes a predictable change in the reflectivity of the light reflective surface;
    temperature sensing means for sensing the temperature of the light reflective surface at two or more distinct positions on the light reflective surface;
    light source means for irradiating the light reflective surface;
    optical heat source means for providing heat to the light reflective surface; and
    light detecting means for sensing the reflectivity of the light reflective surface.

3. An optical oxygen sensing device of claim 2 wherein said oxidizable material having a light reflective surface comprises palladium metal or a palladium alloy.

4. An optical sensing device of claim 2 wherein the light reflective surface comprises thin film islands of palladium metal, each island about 100 Angstroms in diameter and about 15 Angstroms thick, a total of said islands covering approximately about one to about ten percent of the supporting surface area.

5. An automobile having an internal combustion engine control system operating with lead air-to-fuel ratios comprising an optical oxygen sensing device of claim 2.

6. An optical oxygen sensing device, for highly precise, fast response oxygen partial pressure determinations within automobile exhaust gases for use within internal combustion engine control systems operating with lean air-to-fuel ratios, comprising:
    a film of an oxidizable material having a light reflective surface which reversibly reacts with oxygen gas in accordance with a temperature-oxygen partial pressure relationship to form an oxide of said material, the oxidation of said material causes a predictable change in the reflectivity of the light reflective surface;
    a translucent or transparent ceramic substrate, for providing structural support to the light reflective surface;
    temperature sensing means for sensing the temperature of the light reflective surface at two or more distinct locations on the light reflective surface;
    three way optical system comprising (1) light source means for irradiating the light reflective surface, (2) heat source means having a light beam for providing heat to the light reflective surface, and (3) light detecting means for sensing reflected light from the light reflective surface; and an optical fiber positioned to provide the means for transmission of the three light beams, the light source beam to the light reflective surface, the heat source to the light reflective surface, and the reflected light from the light reflective surface to the light detecting means.

7. An optical oxygen sensing device of claim 6 wherein said film of said oxidizable material having a light reflective surface comprises palladium metal or a palladium alloy.

8. An optical oxygen sensing device of claim 6 wherein the light reflective surface comprises islands of palladium metal, about 50 Angstroms thick and about 100 Angstroms in diameter, a total of said islands covering approximately about one to about ten percent of the supporting surface area.

9. An optical oxygen sensing device of claim 6 further comprising:

means responsive to the reflectance of the light reflective surface for controlling and varying the temperature of the light reflective surface depending on the oxygen partial pressure of the measuring gas, so that a fixed boundary is maintained between a first portion of said oxidizable material which is unoxidized and having a first reflectance and a second portion of said oxidizable material which has been oxidized by the oxygen and having a second reflectance.

10. An optical sensing device of claim 6 further comprising:

means responsive to the reflectance of the light reflective surface for controlling and maintaining the temperature of the light reflective surface so that a constant thermal gradient on the light reflective surface is provided, such that a boundary exists between a first portion of said oxidizable material which is unoxidized and a second portion of said oxidizable material which has been oxidized by the oxygen, said boundary will shift dependent on the varying oxygen partial pressure of the measuring gas.

* * * * *